United States Patent
Van Der Weegen

(10) Patent No.: US 6,719,687 B1
(45) Date of Patent: Apr. 13, 2004

(54) VAGINAL SPECULUM WITH SEAL

(75) Inventor: Clemens Van Der Weegen, Strathfield (AU)

(73) Assignee: S.S.H. Medical Limited, Sydney (AU)

( * ) Notice: Subject to any disclaimer, the term of this patent is extended or adjusted under 35 U.S.C. 154(b) by 0 days.

(21) Appl. No.: 09/980,732
(22) PCT Filed: Mar. 30, 2000
(86) PCT No.: PCT/AU00/00267
§ 371 (c)(1),
(2), (4) Date: Oct. 26, 2001
(87) PCT Pub. No.: WO00/64329
PCT Pub. Date: Nov. 2, 2000

(30) Foreign Application Priority Data

| Apr. 28, 1999 | (AU) | PQ0034 |
| May 7, 1999 | (AU) | PQ0233 |

(51) Int. Cl.⁷ .............................................. A61B 1/00
(52) U.S. Cl. .................................................... 600/184
(58) Field of Search ..................... 604/279; 600/135, 600/184, 201, 210, 220, 235; 606/119

(56) References Cited

U.S. PATENT DOCUMENTS

| 5,217,466 A | * | 6/1993 | Hasson | 606/119 |
| 5,397,312 A | * | 3/1995 | Rademaker et al. | 604/218 |
| 5,451,208 A | * | 9/1995 | Goldrath | 604/515 |
| 5,624,399 A | * | 4/1997 | Ackerman | 604/103.03 |
| 6,132,406 A | * | 10/2000 | Muzzammel | 604/279 |
| 6,156,006 A | * | 12/2000 | Brosens et al. | 604/104 |
| 6,190,365 B1 | * | 2/2001 | Abbott et al. | 604/279 |
| 6,423,038 B1 | * | 7/2002 | Vancaillie | 604/279 |
| 6,468,245 B2 | * | 10/2002 | Alexandersen | 604/105 |
| 6,485,410 B1 | * | 11/2002 | Loy | 600/135 |
| 6,503,192 B1 | * | 1/2003 | Ouchi | 600/114 |
| 2002/0019613 A1 | * | 2/2002 | Alexandersen | 604/279 |

FOREIGN PATENT DOCUMENTS

| WO | WO 00/22974 | 4/2000 |

* cited by examiner

Primary Examiner—Beverly M. Flanagan
(74) Attorney, Agent, or Firm—Cowan Liebowitz & Latman; Mark Montague

(57) ABSTRACT

A vaginal speculum of the kind including a tubular probe (6) for penetrating the vagina wherein the probe is encircled by an annular sealing element (13), in the form of a thick walled, domed shell of polyethylene foam, spaced from the leading end of the probe and which seals only against a circumferential zone of the internal tissue defining the vaginal orifice. The external surface of the sealing element is shaped as a surface of revolution wherein the diameter of the sealing surface increases progressively with axial distance from the leading end of the sealing element and wherein the rate of increase diminishes progressively with said axial distance. The seal therefore provides a low-pressure seal over a limited range of depths of penetration of the probe into the vagina and over a range of angular alignments of the probe.

6 Claims, 5 Drawing Sheets

VAGINAL SPECULUM WITH SEAL

TECHNICAL FIELD

This invention relates to vaginal speculums used for at least the examination of at least the cervical area of the vagina. Essentially such speculums comprise a tubular probe able to be inserted into the vaginal barrel through the vaginal orifice, to define a line of sight extending through the orifice, and associated external equipment.

BACKGROUND ART

As is well known the examination may be made by the naked eye or by means of an optical or electronic camera.

As is also well known, preferred embodiments of vaginal speculums may also provide access to the interior of the vaginal barrel for surgical instruments, such as, for example, tissue samplers for collecting cells for so called pap smear tests as used to detect the onset of cervical cancer.

To facilitate examination of the cervical area and the operation of such instruments it has been suggested that vaginal speculums should allow for inflation of at least the cervical end portion of the vaginal barrel by air or other transparent fluid. This requires the speculum to seal off at least that part of the vaginal barrel to be inflated, a transparent fluid tight septum or plug within the bore of the speculum to prevent outflow of pressurising fluid therethrough and the provision of fluid supply means for the admission of pressurised fluid either to the bore of the speculum ahead of that septum or plug or directly into the sealed off part of the vaginal barrel.

Thus a fully functional vaginal speculum is a complex instrument comprising not only the actual tubular probe which enters the vagina but also said external equipment which may include a hand piece for manipulation of the probe, an eye piece to enable an operator to aim and position the probe, a light source for illuminating the cervical area, a camera or at least means for attaching a camera, supply means for the supply of pressurised transparent fluid, commonly air, and sealing means for the retention of the air or other fluid under pressure within the vaginal barrel.

It is of course essential for at least the tubular probe to be sterile before it is inserted into the vagina. Thus it is customary for the tubular probe to be readily separable from and attachable to the external equipment, either to permit it being sterilised between operations or, more preferably, disposed of at the end of an operation and replaced by a previously unused probe for the next operation.

International Application PCT/AU97/00732 (Superior Spec Holdings Limited) (International Publication No. WO 98/19590), describes a prior known vaginal speculum displaying embodiments of the various features mentioned above.

That prior art speculum includes a single use, disposable tubular probe furnished with an inflatable seal positioned at the leading end of the probe. In clinical trials of that prior art speculum it proved to be generally satisfactory but it was found that the centralising effect of the seal caused some difficulty in examining off-centre areas of the vaginal barrel. Indeed, in rare instances, the cervix itself may be misplaced to an extent making it difficult to examine.

DISCLOSURE OF INVENTION

An object of the present invention is to alleviate the problems associated with a seal at or near the leading end of the tubular probe.

The invention attains that object by providing a vaginal sealing element encircling the tubular probe intermediate its ends, which element is shaped to contact and seal against body tissue defining the vaginal orifice. This positioning of the seal leaves more of the vaginal barrel available for inspection than was the case when using prior known seals and, more importantly, allows more ready positioning of the leading end of the probe, and thus more ready aiming of the line of sight, with respect to the cervix. As the sealing element in speculums according to the invention contacts tissue that is outside the vaginal barrel it is referred to as an external vaginal seal hereinafter even though the tissue in question is not the skin of the woman being examined.

A seal for use in a somewhat analogous situation is disclosed in German Patent Specification No. DE 44 04 253 relating to an anal speculum. In that instance an anal seal in the form of a trumpet mouth or flared skirt having concave sides with a generally radially extending margin is used. In this instance the seal is more fully external than said vaginal external seals characteristic of the present invention, in that at least the radially extending margin of the sealing element contacts the skin surrounding the anus of the person being examined. In experiments leading to the present invention it was found that sealing elements of the shape disclosed in that German specification are not practicable for use in relation to vaginal speculums.

The problems relating to external seals for vaginal speculums arise from the considerable variation in the size and shape of the vaginal orifice as between one woman and another. If a sealing element having a radially projecting margin adapted to contact and seal against the skin around the vaginal orifice were to be used, then that sealing element would practically determine the extent to which the speculum probe enters the vagina. However, because of internal size variation of the vagina from woman to woman, the depth of probing has to be adjusted by the operator to bring the tip of the probe to an appropriate distance from the cervix. While the body size of the woman and the external appearance of the vagina enables an experienced operator to estimate approximately the likely length of probe needed in any instance, the fact remains that exact adjustment of the probe depth cannot be accurately determined before insertion (and consequent contamination preventing re-use of the probe) has been effected. It follows that the seal has to be maintained over a limited range of probe depths, which is incompatible with a seal between a radially extending margin of the sealing element and the external body surface surrounding the vaginal orifice.

The invention overcomes the above mentioned problem by providing a sealing element that is positioned as aforesaid on the tubular probe so as to be external of the vaginal barrel when in use and which seals only against a circumferential zone of the internal tissue defining the vaginal orifice. To that end the sealing element is devoid of a radially extending edge margin and has a sealing surface shaped as a surface of revolution wherein the diameter of the sealing surface increases progressively with axial distance from the leading end of the sealing element and wherein the rate of increase diminishes progressively with said axial distance.

A sealing element according to the invention relies upon the natural resilience of the so-called PC muscle surrounding the vaginal orifice to permit the orifice to expand and contract so as to allow penetration of the sealing element into the orifice and the maintenance of a seal therewith, throughout a limited range of depths of penetration.

Therefore the invention consists in a vaginal speculum of the kind including a tubular probe for penetrating the vagina characterised in that said probe is encircled by an annular sealing element spaced from the leading end of the probe which seals only against a circumferential zone of the internal tissue defining the vaginal orifice and is shaped as a surface of revolution wherein the diameter of the sealing surface increases progressively with axial distance from the leading end of the sealing element and wherein the rate of increase diminishes progressively with said axial distance.

More simply stated, preferred embodiments of the sealing element may be described as a convex dome devoid of a radially extending edge margin, and having a central circular opening through which the tubular probe tightly extends.

BRIEF DESCRIPTION OF THE DRAWINGS

By way of example, an embodiment of the above-described invention is described hereinafter with reference to the accompanying drawings.

BEST MODE OF CARRYING OUT THE INVENTION

Figure 1:
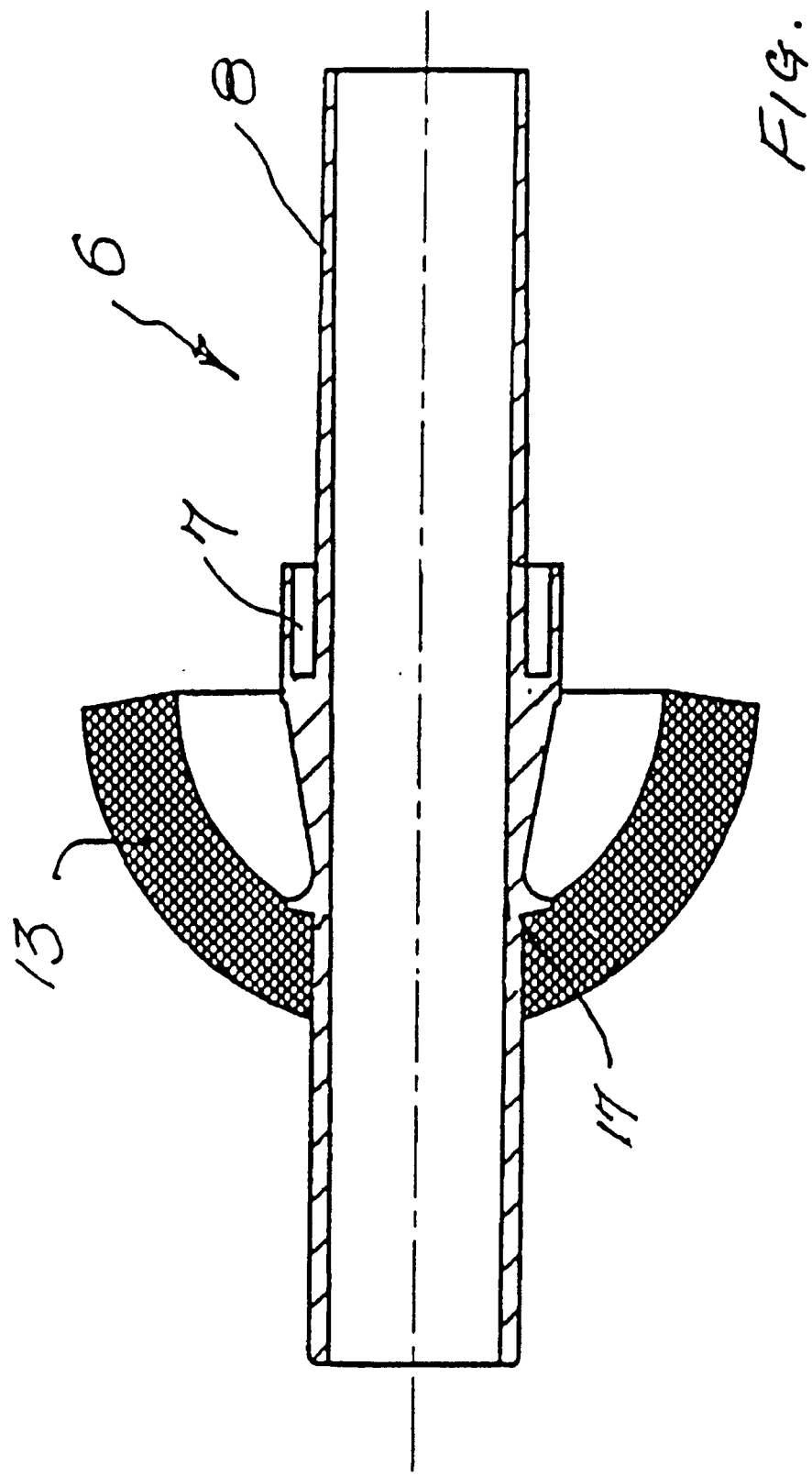
FIG. 1 is a longitudinal sectional view of a tubular vaginal probe and external sealing element characteristic of vaginal speculums according to the invention.
Figure 2:
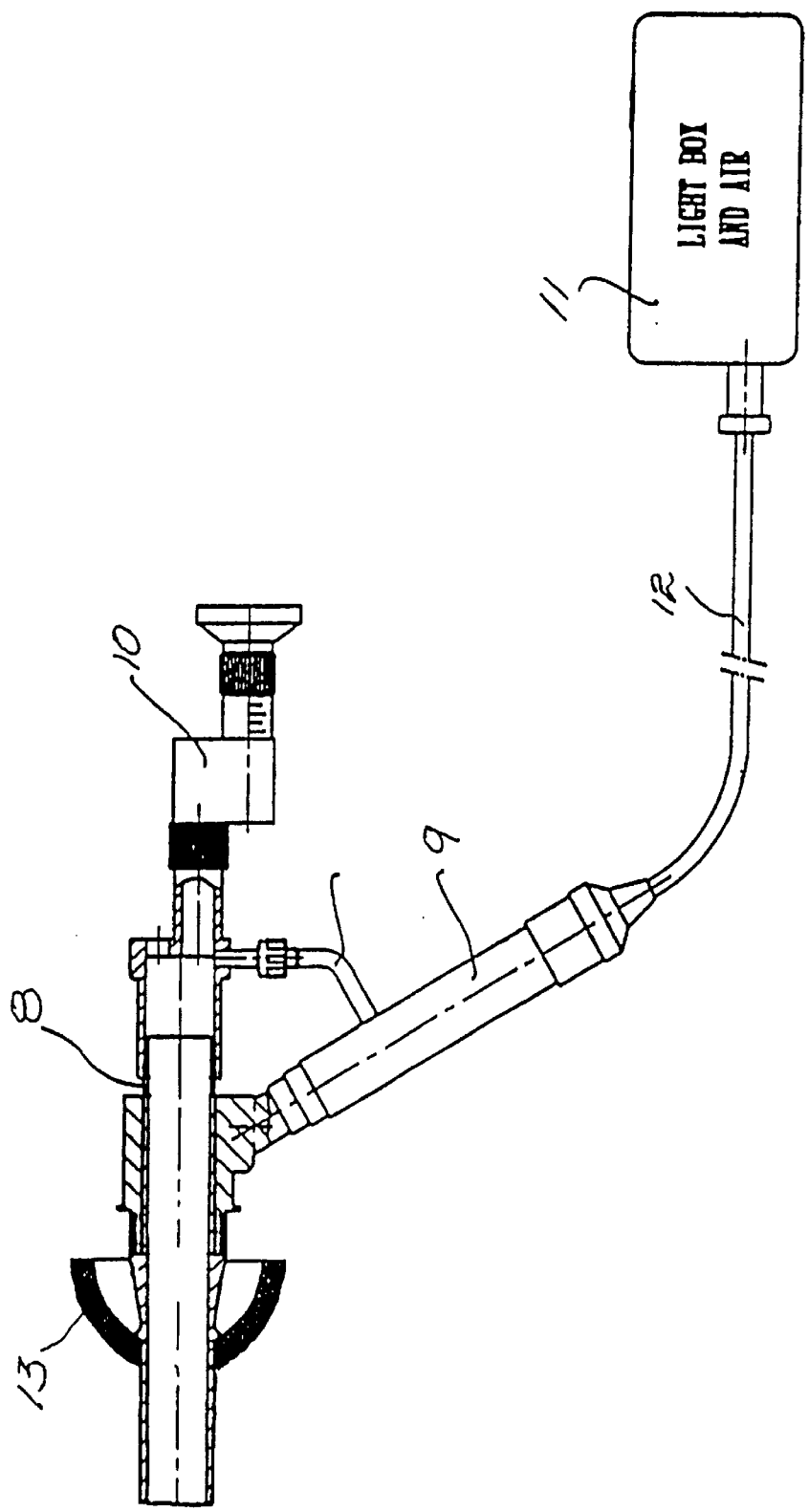
FIG. 2 is a partly sectioned view of the probe and sealing element of FIG. 1 shown assembled to typical conventional components of a vaginal speculum.
Figure 4:
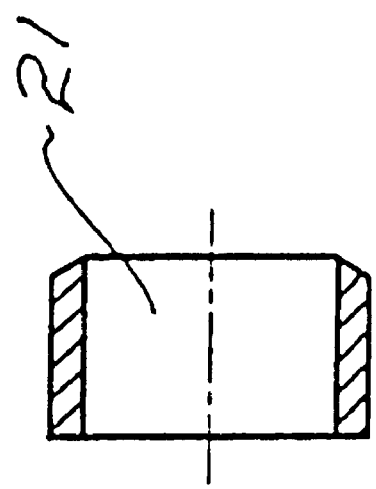
FIG. 4 is a longitudinal sectional view of the spacer of FIG. 2
Figure 3:
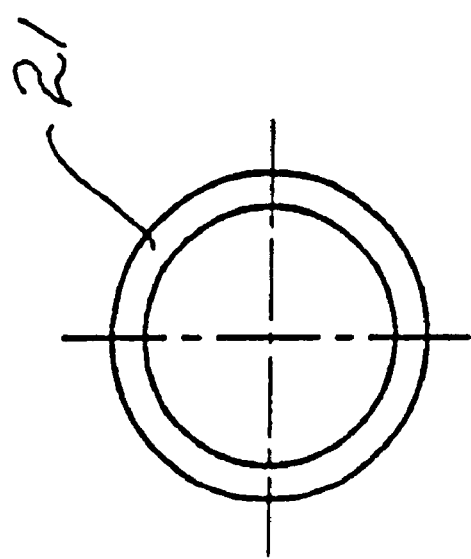
FIG. 3 is an end view of a spacer.

In FIG. 1 there is shown a disposable tubular probe 6 of a vaginal speculum. The probe 6 is adapted by means of a conventional collar 7 and slightly tapered trailing end spigot 8 to be plugged into a conventional hand piece 9 (see FIG. 2) for manipulation of the probe, an eye piece 10 to enable an operator to aim the probe and directly view the cervical area of the vagina and an enclosure 11 for a light source and air pump. The enclosure 11 is connected to the hand piece by a flexible tube 12. An optical fibre cable extends through the tube 12 enabling the cervical area of the vagina to be illuminated by light travelling along that cable and through the transparent walls of the probe 6. Pressurised air from the pump also flows along the tube 11 into the interior of the hand piece 9 and thence through air supply means 13 into the bore of the probe 6. The air supply rate can be regulated by the user of the speculum. The eyepiece 10 also seals the trailing end of the probe to prevent leakage of air from that end.

Insofar as described above the subject matter of FIGS. 1 and 2 is previously known, however the illustrated speculum further comprises a novel sealing element 13 which provides considerable advantages over the prior art.

Figure 5:
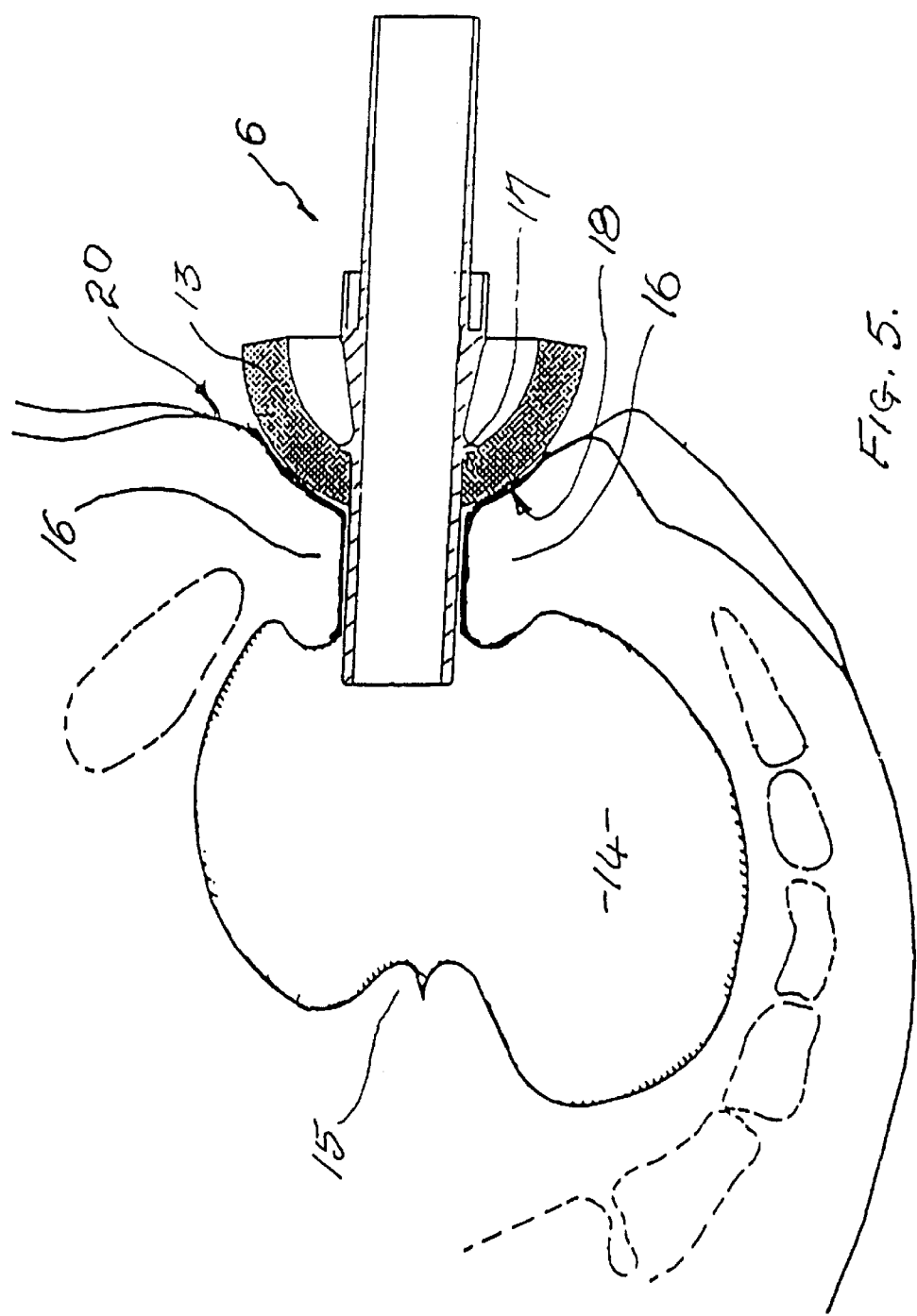
FIG. 5 is a sectional view through an inflated vagina and a tubular probe and sealing element characteristic of speculums according to the invention inserted thereinto.
Figure 6:
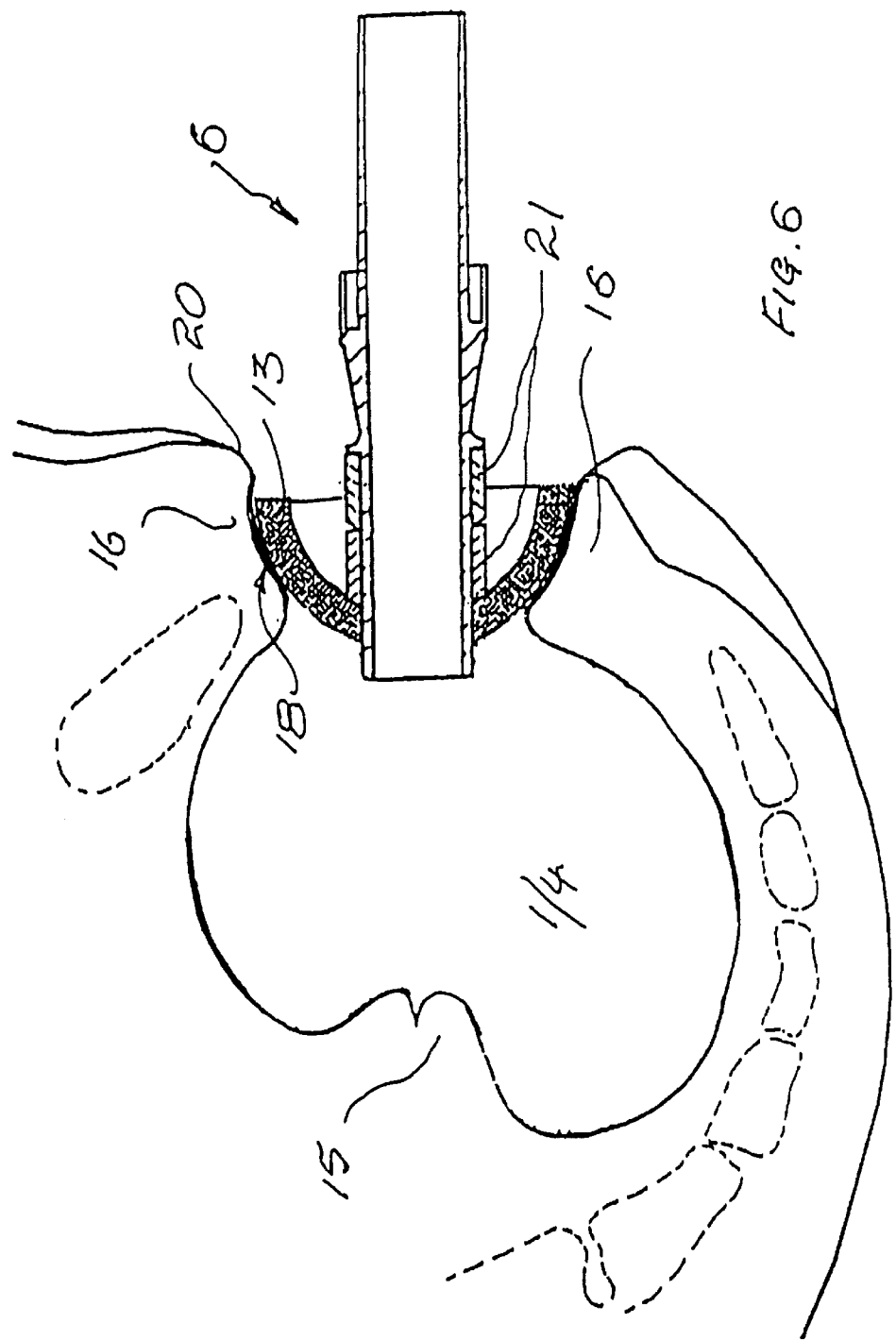
FIG. 6 a view similar to FIG. 5 wherein the vagina has a relatively larger or more relaxed vaginal orifice.

FIGS. 5 and 6 show an inflated vaginal barrel 14 with the cervix 15 at its inner end and its orifice defined at its outer end by the annular sphincter muscle 16 known as the PC muscle.

In accordance with this embodiment of the invention the element 13 is a thick walled hollow hemisphere of closed cell, dense polyethylene foam with a hole at its centre through which the probe 6 tightly extends. The sealing element 13 is prevented from sliding along the probe to the right as seen in FIGS. 1 and 5 by an annular abutment 17 integral with the probe 6.

It will be seen that in FIG. 5 the sealing element 13 has been obtruded partly through the PC muscle so as to distend a front portion of the vaginal orifice and make sealing contact with an annular zone 18 of the normally internal surface of the vaginal orifice. It should be mentioned that this seal is not a high pressure seal such as could arise if a radially extending flange on the sealing element were to be pushed too firmly by an operator against the external zone 20 encircling the orifice. This constitutes an important safety measure against over pressurising the barrel 14. In the event of excess pressure the zone 18 simply expands further to allow pressurising fluid to escape.

FIG. 6 shows a vagina whereby due to natural variation or loss of muscle tone due to age or previous childbirths, the vaginal orifice is enlarged or the PC muscle is more than usually relaxed. The operator, having regard to those factors may position one or more tubular spacers 21 on the probe 6 (see FIG. 6) before assembling the sealing element 13 thereto. Thus the greater intrusion of the sealing element 13 into the vaginal orifice that is needed to arrive at a satisfactory seal in such instances may be accommodated with the tip of the probe 6 still at a required distance from the cervix 15.

Furthermore, as a result of the shape of the sealing element 13 a low-pressure seal is maintained over a range of angular adjustment of the probe as may be needed to bring the line of sight into register with the cervix.

What is claimed is:

1. A vaginal speculum of the kind including a tubular probe for penetrating the vagina characterized in that said probe is encircled by an annular sealing element spaced from a leading end of the probe which has a sealing surface which seals only against a circumferential zone of the internal tissue defining the vaginal orifice and is shaped as a surface of revolution wherein a diameter of the sealing surface increases progressively with an axial distance from a leading end of the sealing element and wherein a rate of increase diminishes progressively with said axial distance.

2. A vaginal speculum according to claim 1 where said sealing element is a dome shaped shell having a central hole through which said tubular probe tightly extends in the axial direction of the dome.

3. A speculum according to claim 2, wherein said shell is made of a closed cell plastics foam.

4. A speculum according to claim 3 wherein said plastics foam is polyethylene.

5. A speculum according to claim 1 wherein the position of the sealing element on the tubular probe is determined by an abutment on the probe integral therewith.

6. A speculum according to claim 5 in speculum with one or more spacers encircling the probe between the seal sealing element and the abutment.

* * * * *